US005788463A

United States Patent [19]
Chan

[11] Patent Number: 5,788,463
[45] Date of Patent: Aug. 4, 1998

[54] MANUAL VACUUM PRODUCING SYSTEM HAVING PRESSURE INDICATOR

[76] Inventor: Kwan-Ho Chan, 4803 1st Pl., Lubbock, Tex. 79416

[21] Appl. No.: 577,698

[22] Filed: Dec. 22, 1995

[51] Int. Cl.⁶ .............................. F04B 21/00; F04B 21/04
[52] U.S. Cl. ....................... 417/63; 417/53; 417/553; 73/730
[58] Field of Search .................. 417/63, 553, 53; 73/730

[56] References Cited

U.S. PATENT DOCUMENTS

| | | | |
|---|---|---|---|
| 2,689,533 | 9/1954 | Ericson | 417/555.1 |
| 3,240,207 | 3/1966 | Barker et al. | 73/730 |
| 3,563,095 | 2/1971 | Robinson, Jr. | 73/730 |
| 3,752,604 | 8/1973 | Dorn | 417/553 |
| 4,404,924 | 9/1983 | Goldberg et al. | 92/92 |
| 4,702,675 | 10/1987 | Aldrovandi et al. | 73/730 |
| 4,951,509 | 8/1990 | Yamauchi | 73/730 |
| 4,975,028 | 12/1990 | Schultz | 417/553 |
| 5,299,917 | 4/1994 | Schultz | 417/553 |
| 5,380,175 | 1/1995 | Amarume | 417/553 |
| 5,533,879 | 7/1996 | Chen | 417/553 |

FOREIGN PATENT DOCUMENTS 96466  12/1960  Netherlands ........................ 417/553

*Primary Examiner*—Charles G. Freay
*Attorney, Agent, or Firm*—Pandiscio & Pandiscio, P.C.

[57] ABSTRACT

A vacuum system comprising a vacuum pump and a vacuum indicator. The vacuum pump comprises a cylinder, a piston disposed in the cylinder, a piston rod fixed to the piston and extending through an end of the cylinder, the rod being movable reciprocally, a sealing ring disposed on and around the piston and in engagement with an inside wall of the cylinder, and stops extending radially outwardly from the piston, the stops including a proximal stop and a distal stop, the sealing ring being axially movable between the proximal and distal stops, the piston having an axially-extending groove therein, the groove extending from proximal of the distal stop to proximal of the proximal stop, whereby upon movement of the piston in a first direction, the sealing ring engages the distal stop and seals an annular space between the piston and the inside wall of the cylinder, and upon movement of the piston in a second direction, the sealing ring engages the proximal stop and leaves unobstructed the axially-extending groove. The vacuum indicator comprises an elongated tubular member for disposal in a vacuum line between the vacuum pump and a housing which is to be evacuated, the tubular member being made of an elastic material, with a wall of the tubular member having a uniform thickness of greater than ⅕ of an inside radius of the tubular member.

5 Claims, 9 Drawing Sheets

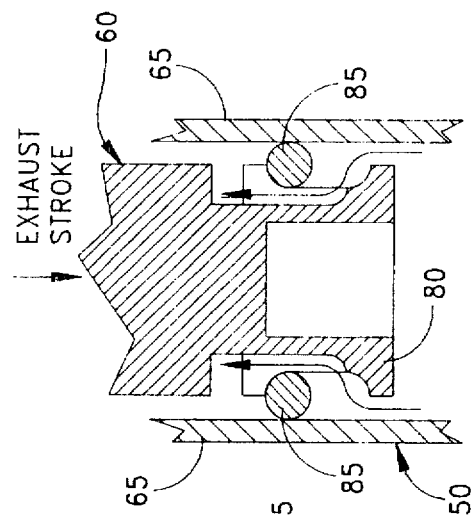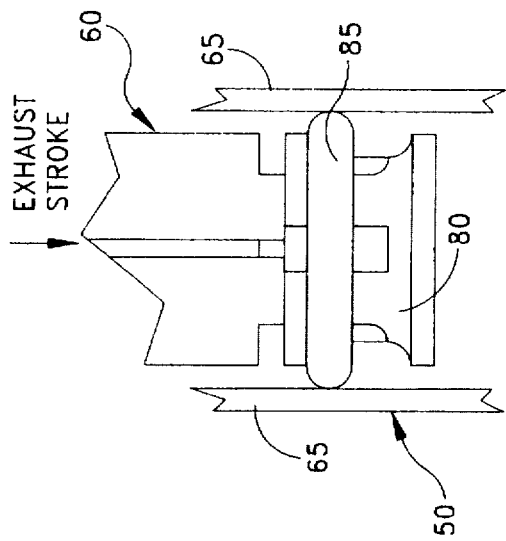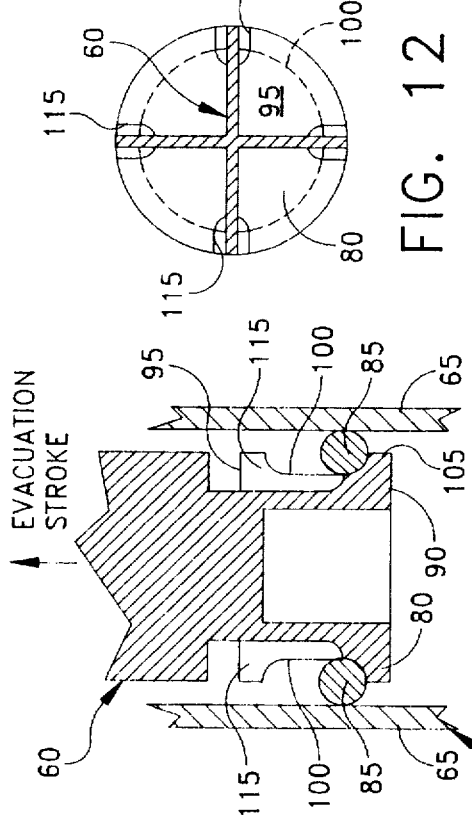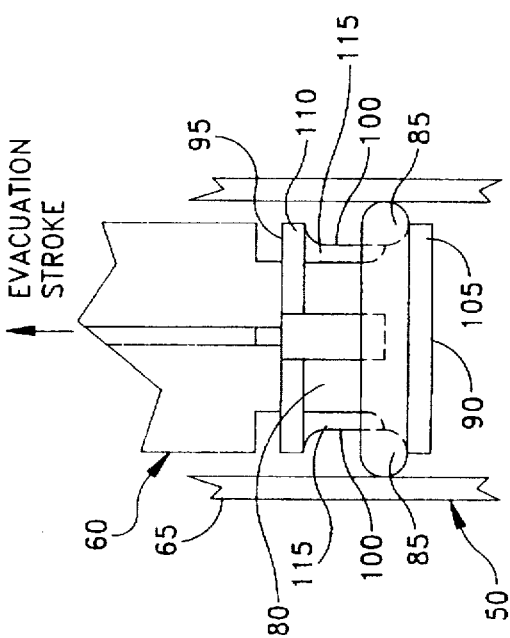

MANUAL VACUUM PRODUCING SYSTEM HAVING PRESSURE INDICATOR

FIELD OF THE INVENTION

This invention relates to vacuum systems in general, and more particularly to vacuum systems of the sort which are particularly well suited for use in connection with bone cement mixing systems.

BACKGROUND OF THE INVENTION

In many situations it is necessary, or at least desirable, to create a vacuum within a container or vessel.

For example, in many orthopaedic surgical procedures, bone cements are used to fix implants to bone. Conventional bone cements are generally polymeric materials which are prepared by copolymerizing the cement's constituent components as the cement is needed during the surgical procedure. More particularly, such bone cement is typically prepared by copolymerizing a liquid monomer and a powdered copolymer, e.g., methyl methacrylate and polymethyl methacrylate ("PMMA"), or methyl methacrylate and styrene. Unfortunately, it has been found that as the cement's constituent components are mixed together to effect the aforementioned copolymerization, air bubbles are generally introduced into the cement. The presence of these air bubbles increases the porosity of the cement and thereby undermines its structural integrity. Fortunately, it has also been found that the strength of the cement can be significantly increased if the air bubbles are eliminated from the mixture. Consequently, the constituent components of the bone cement are ideally mixed in a vacuum.

More particularly, it has been found that conventional mixing of PMMA bone cement produces a porosity of between about 5 and 6 percent in the hardened cement. Conversely, mechanical mixing under vacuum can reduce the cement's porosity to between about 0.1 and 0.8 percent. This results in an increase of about 24 percent in compressive strength, about 23 percent in diametrical tensile strength, and about 44 percent in uniaxial tensile strength.

In addition to the foregoing, it has also been found that the level of vacuum used during mixing is critical to achieving optimal results. More particularly, it has been found that the level of vacuum provided by a standard operating room wall source (typically about 200–400 mm Hg) is generally insufficient to adequately remove porosity from the cement mixture. Empirically, it has been determined that a vacuum level of about 500–550 mm Hg below atmospheric level yields satisfactory results.

In view of the foregoing, vacuum systems have been developed for use in mixing bone cement. These vacuum systems generally include vacuum pumps for creating the desired vacuum within the container or vessel which is used to mix the bone cement, and vacuum indicators for indicating when the proper level of vacuum has been created in that container or vessel.

Unfortunately, the vacuum pumps generally associated with bone cement vacuum systems are either relatively large in size or fairly complex in design, or both. Furthermore, such vacuum pumps are generally too expensive to be considered disposable at the conclusion of a surgical procedure. As a result, problems of cleaning, reassembly and/or sterilization may arise.

Furthermore, the vacuum indicators generally associated with bone cement vacuum systems are generally either relatively complex mechanical or electromechanical gauges adapted to provide a pressure readout on a front display or panel, or plastic "drip chamber" vacuum indicators of the sort which will deform inwardly according to the pressure differential established between the chamber's inside and outside environments.

Unfortunately, current mechanical or electromechanical vacuum gauges suffer from the fact that they are generally too expensive to be considered disposable at the conclusion of the surgical procedure. As a result, problems of cleaning, reassembly and/or sterilization may arise.

Vacuum indicators formed out of plastic drip chambers in turn suffer from their own set of deficiencies. More particularly, these plastic drip chamber vacuum indicators are formed using drip chambers of the sort typically found in intravenous (IV) lines. The drip chamber is connected to the cement mixing container on one end and to the vacuum pump on the other end, whereby the same level of vacuum will be present in the drip chamber as in the cement mixing container. The outside of the drip chamber is exposed to the ambient atmosphere. As a result of this construction, as the vacuum pump pulls a vacuum in the cement mixing container, and hence in the plastic drip chamber as well, the side wall of the drip chamber will gradually deform according to the pressure differential created between the drip chamber's inside and outside environments. This allows the user to see when a vacuum has been created within the drip chamber, and hence within the cement mixing container.

Unfortunately, vacuum indicators formed out of plastic drip chambers suffer from the fact that they are able to convey only limited information to the user. More particularly, these drip chamber vacuum indicators are generally made out of a plasticized polyvinylchloride ("PVC") or polyvinylacetate or polyvinylalcohol or a similar material. As a result, the drip chamber generally undergoes progressive deformation with increasing vacuum, starting at about 350 mm Hg below atmospheric pressure. Due to the gradual and progressive nature of this deformation, the plastic drip chamber vacuum indicator can only serve as a qualitative vacuum indicator, i.e., it will show if a vacuum has been established, but it will not indicate the exact level of that vacuum.

Plastic drip chamber vacuum indicators also suffer from the fact that they do not perform reliably over several cycles. More particularly, when a first vacuum is pulled and then released, the deformed wall of the drip chamber vacuum indicator will generally take several minutes to return its former tubular shape. At times the drip chamber vacuum indicator may not even completely return to its original tubular shape. If vacuum is then applied to the system a second time, the drip chamber vacuum indicator may begin to deform at a different (i.e., lower) pressure differential than the first time. This can cause confusion and/or error on the part of the user.

OBJECTS OF THE INVENTION

Accordingly, one object of the present invention is to provide a new and improved vacuum system for creating a vacuum within a container or vessel.

Another object of the present invention is to provide a new and improved vacuum system which is particularly well suited for use in connection with bone cement mixing systems.

And another object of the present invention is to provide a new and improved vacuum pump.

Still another object of the present invention is to provide a new and improved vacuum pump which is particularly well suited for use in connection with bone cement mixing systems.

3

Yet another object of the present invention is to provide a new and improved vacuum indicator.

And another object of the present invention is to provide a new and improved vacuum indicator which is particularly well suited for use in connection with bone cement mixing systems.

And still another object of the present invention is to provide a new and improved method for creating a vacuum within a container or vessel.

And yet another object of the present invention is to provide a new and improved method for creating a vacuum within a container or vessel in a bone cement mixing system.

SUMMARY OF THE INVENTION

These and other objects of the present invention are achieved by the provision and use of a novel vacuum system which comprises a novel vacuum pump and a novel vacuum indicator.

The novel vacuum pump comprises a cylinder; a piston disposed in the cylinder; a piston rod fixed at a first end to the piston and extending through an end of the cylinder, the rod being movable axially and reciprocally to move the piston in the cylinder axially and reciprocally in first and second opposite directions; a sealing ring disposed on and around the piston and in engagement with an inside wall of the cylinder throughout a periphery of the sealing ring; and stop means extending radially outwardly from the piston, the stop means including proximal stop means proximate a proximal surface of the piston and distal stop means proximate a distal surface of the piston, the sealing ring being axially movable between the proximal and distal stop means; the piston having an axially-extending groove therein, the axially-extending groove extending from proximal of the distal stop means to proximal of the proximal stop means; whereby upon movement of the piston in the first direction, the sealing ring engages the distal stop means and seals an annular space between the piston and the inside wall of the cylinder, and upon movement of the piston in the second direction, the sealing ring engages the proximal stop means and leaves unobstructed the axially-extending groove, such that fluid in the cylinder is prevented from flowing between the piston and the cylinder inside wall when the piston moves in the first direction, and is permitted to flow between the piston and the cylinder inside wall when the piston moves in the second direction.

The novel vacuum indicator comprises an elongated tubular member for disposal in a vacuum line between the vacuum pump and a housing which is to be evacuated, the tubular member being made out of an elastic material, and with a wall of the tubular member having a uniform thickness of greater than 1/5 of an inside radius of the tubular member.

The present invention also includes the use of the novel vacuum pump and novel vacuum indicator to create a vacuum in a container or vessel.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein:

FIG. 12 is a schematic proximal end view of the novel vacuum pump's piston, with the piston rod being shown in section;

FIG. 13 is a schematic side view in section of the novel vacuum pump's piston assembly, with the piston assembly being shown during the vacuum pump's evacuation stroke;

FIG. 14 is a schematic side view of the novel vacuum pump's piston assembly, with the piston assembly being shown during the vacuum pump's evacuation stroke;

FIG. 15 is a schematic side view in section of the novel vacuum pump's piston assembly, with the piston assembly being shown during the vacuum pump's exhaust stroke;

FIG. 16 is a schematic side view of the novel vacuum pump's piston assembly, with the piston assembly being shown during the vacuum pump's exhaust stroke;

DETAILED DESCRIPTION OF THE PREFERRED EMBODIMENTS

Figure 1:
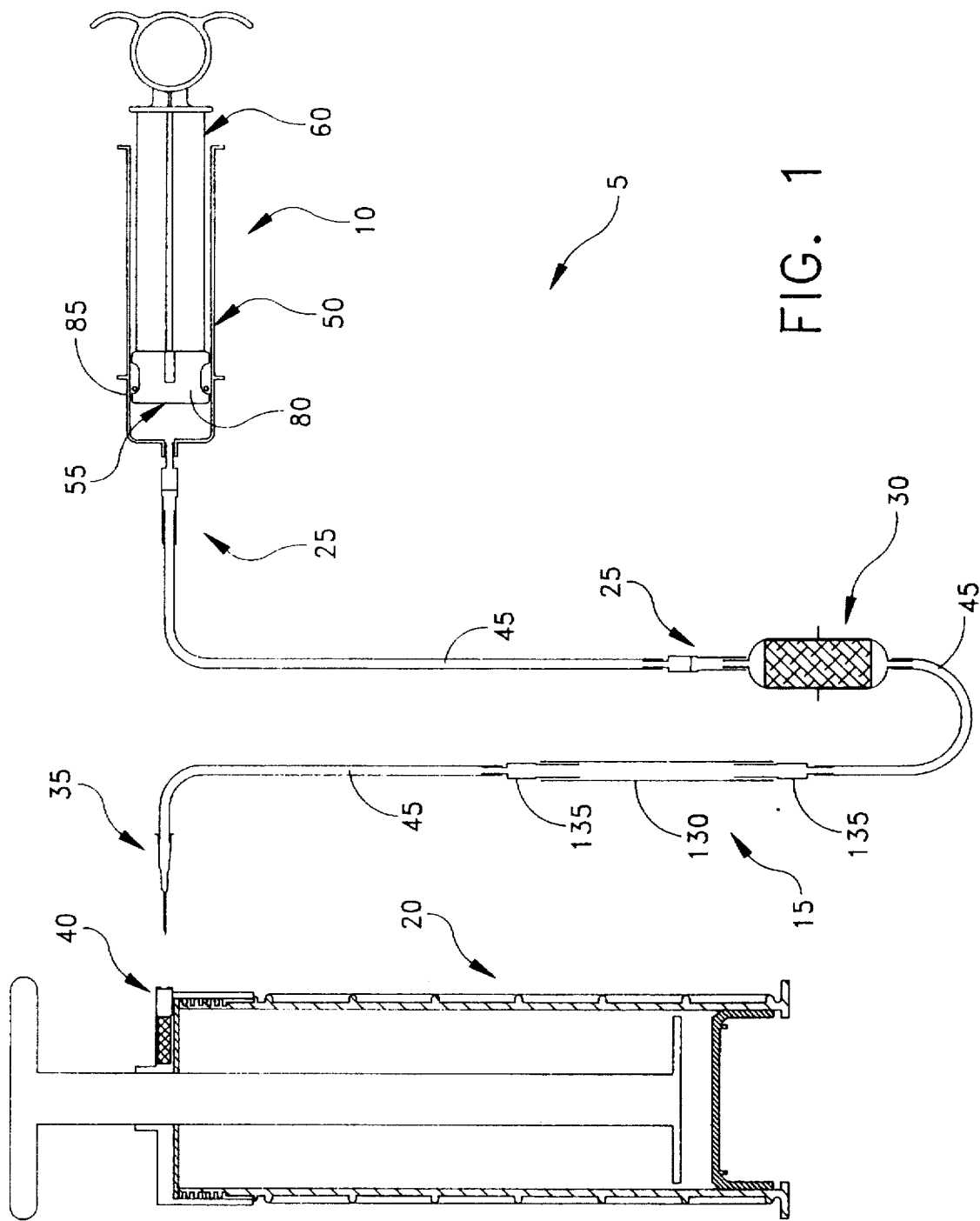
FIG. 1 is a schematic view of a vacuum system formed in accordance with the present invention, wherein the system comprises a novel vacuum pump and a novel vacuum indicator, among other elements.
Figure 2:
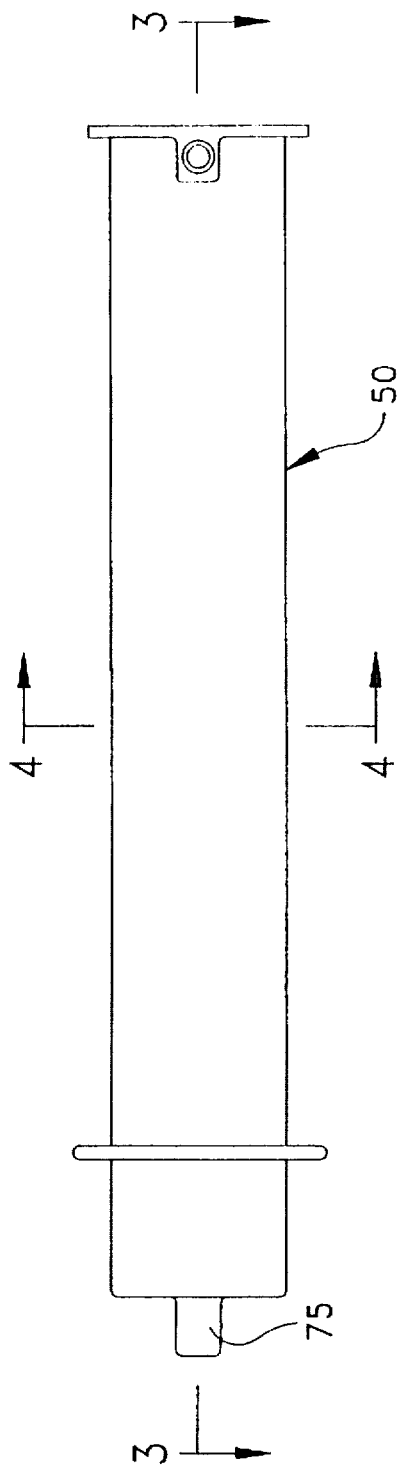
FIG. 2 is a side view in elevation of the novel vacuum pump's cylinder.
Figure 3:
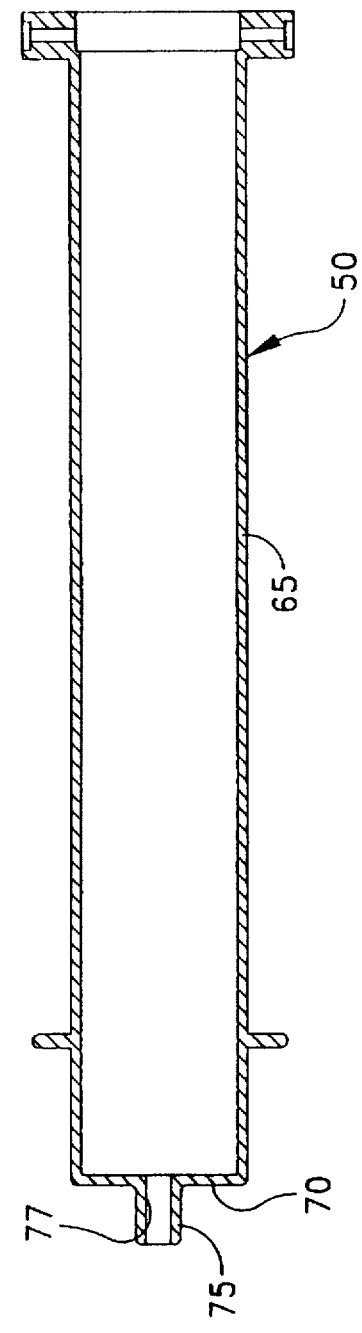
FIG. 3 is a sectional view taken along line 3—3 of FIG. 2.
Figure 5:
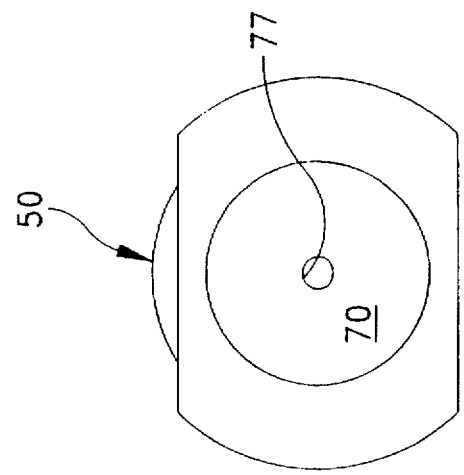
FIG. 5 is a proximal end view of the novel vacuum pump's cylinder.
Figure 4:
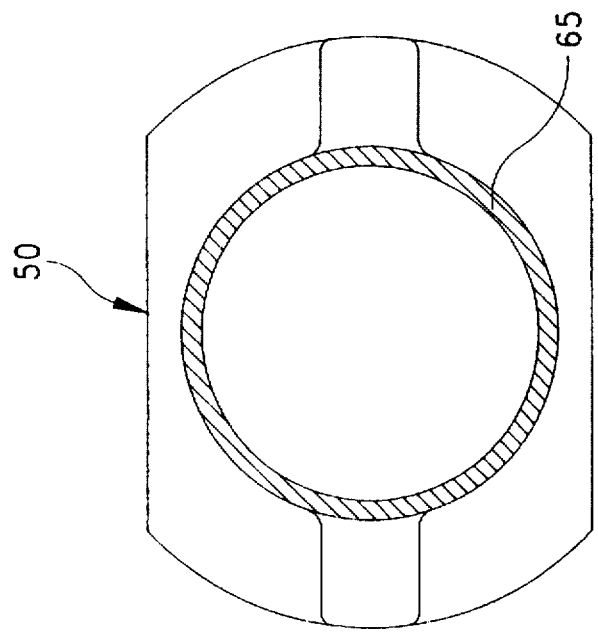
FIG. 4 is a sectional view taken along line 4—4 of FIG. 2.
Figure 6:
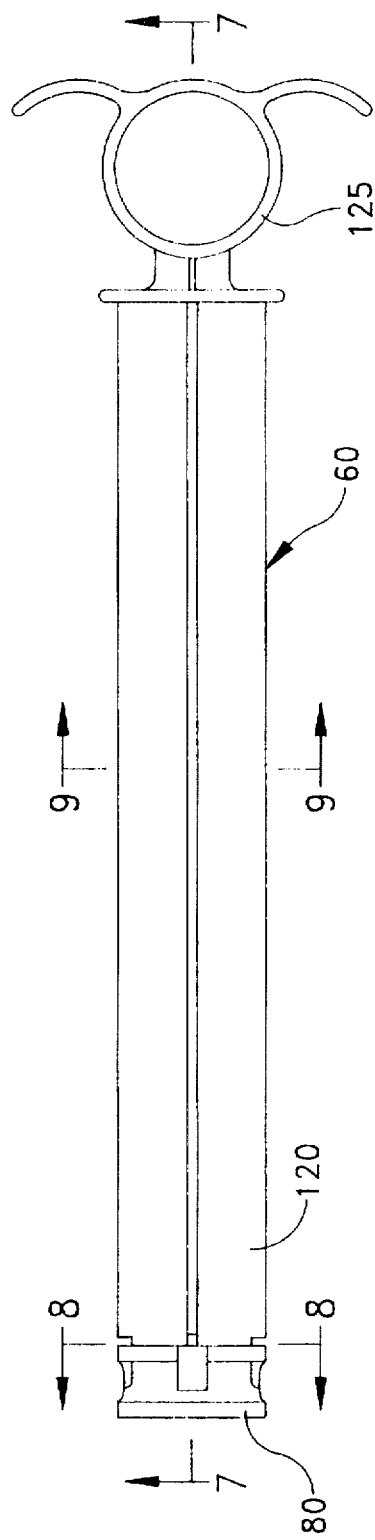
FIG. 6 is a side view in elevation of the novel vacuum pump's piston and piston rod.
Figure 7:
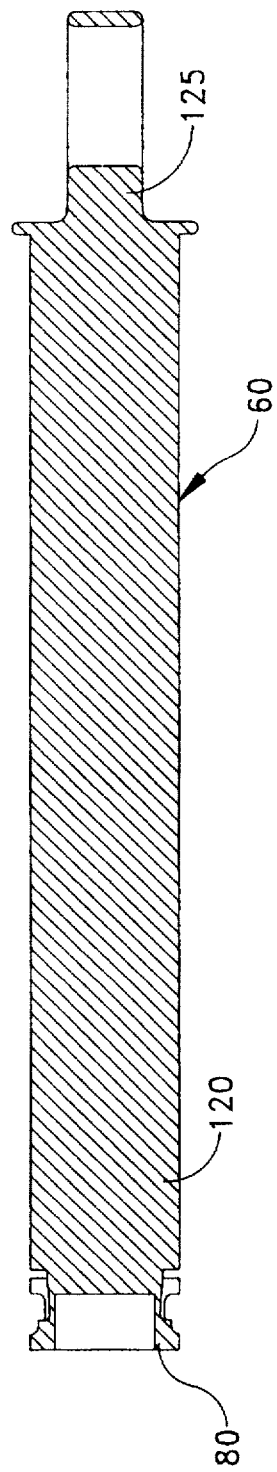
FIG. 7 is a sectional view taken along line 7—7 of FIG. 6.
Figure 11:
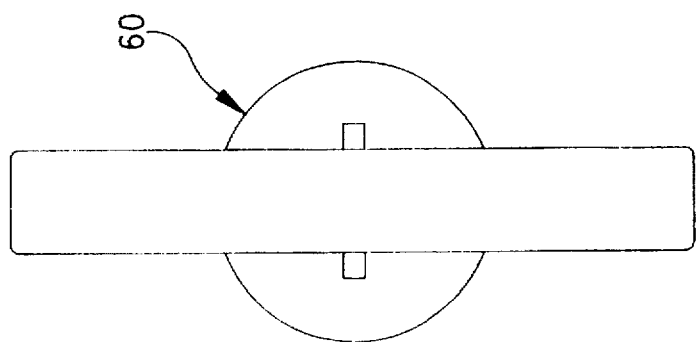
FIG. 11 is a proximal end view of the assembly shown in FIG. 6.
Figure 9:
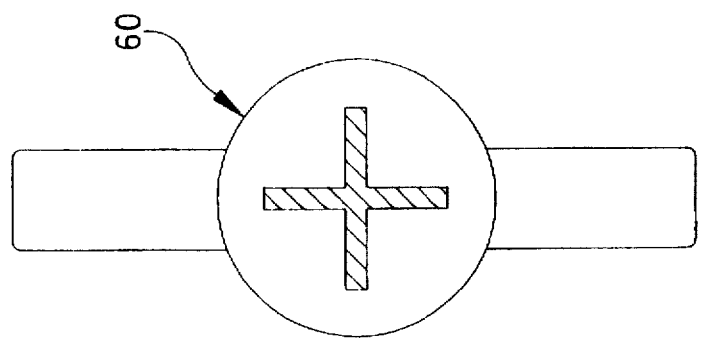
FIG. 9 is a sectional view taken along line 9—9 of FIG. 6.
Figure 8:
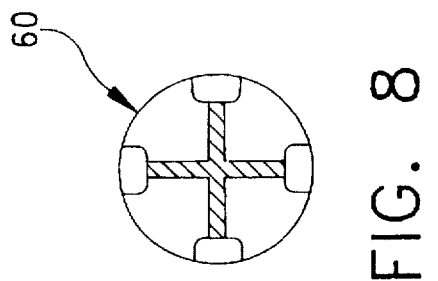
FIG. 8 is a sectional view taken along line 8—8 of FIG. 6.
Figure 10:
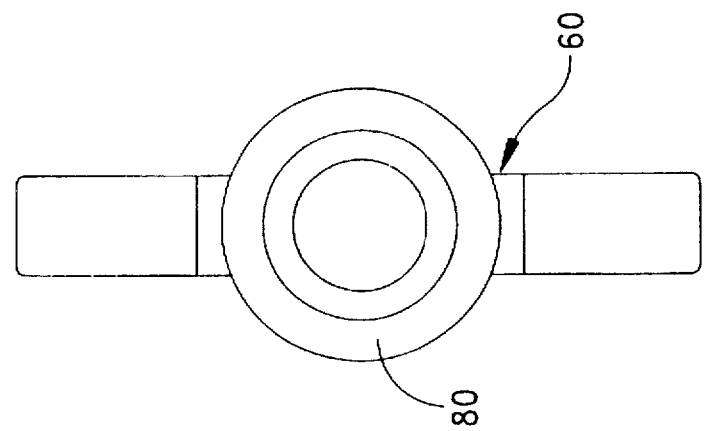
FIG. 10 is a distal end view of the assembly shown in FIG. 6.

Looking first at FIG. 1, there is shown a vacuum system 5 for creating a vacuum within a container or vessel. Vacuum system 5 generally comprises a vacuum pump 10 for creating a vacuum within a container or vessel, and a vacuum indicator 15 for determining when the proper level of vacuum has been created in that container or vessel. While it is envisioned that vacuum system 5 may be used to create a vacuum within a wide variety of different containers or vessels, for a wide range of different applications, one particular aspect of the present invention involves using vacuum system 5 to create a vacuum within a cement mixing container, e.g., the container 20 illustrated in FIG. 1. In connection with such an application, vacuum system 5 preferably also comprises a pair of check valves 25 for preventing backflow of air from vacuum pump 10 into container 20, a filter 30 for preventing selected substances from passing from container 20 into vacuum pump 10, and a connector 35 adapted to make an airtight connection to a corresponding connector 40 provided on container 20. Flexible tubing 45 connects each of the foregoing elements together in series, as will hereinafter be described in further detail.

Looking next at FIGS. 1–16, vacuum pump 10 generally comprises a cylinder 50, a piston assembly 55, and a piston rod 60.

Cylinder 50 is shown in FIGS. 1, 2–5 and 13–16. Cylinder 50 is characterized by a cylindrical side wall 65 (FIG. 3) and a distal wall 70. Distal wall 70 includes a fitting 75. A passageway 77 extends through fitting 75 and distal wall 70.

Piston assembly 55 is shown in FIGS. 1 and 12–16. Piston assembly 55 generally comprises a piston 80 (FIGS. 1, 6, 7, 10 and 12–16) and an O-ring 85 (FIGS. 1 and 13–16). Piston 80 is sized so as to have an outer diameter smaller than the inner diameter of cylinder 50 (FIGS. 13–16), and includes a distal end surface 90 and a proximal end surface 95 (FIGS. 13 and 14).

A circumferentially-extending groove 100 (FIGS. 12–14) is disposed in the outer wall of piston 80. Circumferentially-extending groove 100 is disposed in piston 80 such that (i) a distal annular shoulder 105 (FIGS. 13 and 14) is defined between the distal portion of the circumferentially-extending groove 100 and the piston's distal end surface 90, and (ii) a proximal annular shoulder 110 (FIG. 14) is defined between the proximal portion of the circumferentially-extending groove 100 and the piston's proximal end surface 95. As seen in FIGS. 12–16, the floor of circumferentially-extending groove 100 is substantially cylindrical in configuration, whereby when piston 80 is disposed in cylinder 50, an annular gap of fixed size will be created between the floor of circumferentially-extending groove 100 and the adjacent inside wall of cylinder 50. Stated another way, the floor of circumferentially-extending groove 100 and the inside wall of cylinder 50 will reside in confronting, concentric relation when piston 80 is disposed in cylinder 50.

A plurality of axially-extending grooves 115 (FIGS. 12–14) are disposed in the outer surface of piston 80. Axially-extending grooves 115 intersect circumferentially-extending groove 100 in the manner shown in the drawings. In particular, it is to be appreciated that the distal ends of axially-extending grooves 115 terminate short of the distal end of circumferentially-extending groove 100 (FIGS. 13–16) as will hereinafter be discussed in further detail, while the proximal ends of axially-extending grooves 115 open on the piston's proximal end surface 95 (FIGS. 12–16).

O-ring 85 is disposed in the piston's circumferentially-extending groove 100 (FIGS. 13 and 14). O-ring 85 is sized so that it will make a sliding fit within the piston's circumferentially-extending groove 100, whereby the O-ring can slide from the distal end of the groove (FIGS. 13 and 14) to the proximal end of the groove (FIGS. 15 and 16), and vice versa. At the same time, O-ring 85 is sized so that it will make a frictional fit with the inside surface of the cylinder's side wall 65 (FIGS. 13–16). In essence, O-ring 85 is sized so that it will reside in the annular gap defined by the floor of circumferentially-extending groove 100 and the inside wall of cylinder 50, with the O-ring firmly but smoothly engaging, simultaneously, both the floor of circumferentially-extending groove 100 and the inside wall of cylinder 50. In this way, when piston assembly 55 is moved proximally within cylinder 50, frictional engagement between O-ring 85 and the inside surface of the cylinder's side wall 65 will cause O-ring 85 to seat itself at the distal end of circumferentially-extending groove 100, against the piston's distal annular shoulder 105 (FIGS. 13 and 14). In a corresponding manner, when piston assembly 55 is moved distally within cylinder 50, frictional engagement between O-ring 85 and the inside surface of the cylinder's side wall 65 will cause O-ring 85 to seat itself at the proximal end of circumferentially-extending groove 100, against the piston's proximal annular shoulder 110 (FIGS. 15 and 16). Thus it will be seen that the piston's distal annular shoulder 105 and its proximal annular shoulder 110 essentially form stops for limiting the axial travel of O-ring 85 within the piston's circumferentially-extending groove 100.

In accordance with the present invention, the piston's axial grooves 115 are formed such that the distal ends of the grooves will be closed off by O-ring 85 when the O-ring is seated against the piston's distal shoulder 105 (FIGS. 13 and 14), and the piston's axial grooves 115 will not be closed off by O-ring 85 when the O-ring is seated against the piston's proximal shoulder 110 (FIG. 15 and 16). Thus it will be seen that (i) when O-ring 85 is seated against the piston's distal shoulder 105 (FIGS. 13 and 14), air in cylinder 50 will be prohibited from passing by piston assembly 55, and (ii) when O-ring 85 is seated against the piston's proximal shoulder 110 (FIGS. 15 and 16), air in cylinder 50 will be free to pass by piston assembly 55.

It is to be appreciated that, as a consequence of the foregoing construction, the ability (or inability) of fluid to pass by piston 80 is determined solely by the direction of motion of piston 80 within cylinder 50. It is not determined by the pressure differential existing across O-ring 85. This feature is in marked contrast to many prior art vacuum pumps, where the evacuation and exhaust phases of the pump are determined by the pressure differential existing across a valve element within that pump. With such prior art vacuum pumps, the efficiency of the pump is reduced according to the amount of pressure differential required to "open" and "close" the valve element. Thus, the present invention provides a highly efficient vacuum pump, since it does not rely on a pressure differential to change valve states.

Piston rod 60 is shown in FIGS. 1, 6–11 and 12–16. Piston rod 60 serves to support piston assembly 55 within cylinder 50, and to permit a user to move piston assembly 55 back and forth within cylinder 50, as will hereinafter be described in further detail. Piston rod 60 is characterized by a distal end 120 (FIGS. 6 and 7) which is attached to piston assembly 55, and a proximal end 125 which is adapted to be gripped by the hand of a user. It is to be appreciated that piston rod 60 is formed so that (i) piston assembly 55 can be moved smoothly back and forth along the length of cylinder 50, without parts binding within the cylinder, and (ii) air located on the proximal side of piston assembly 55 is free to pass by piston rod 60 and exit out the proximal end of vacuum pump 10, as will hereinafter be discussed in further detail.

On account of the foregoing construction, when vacuum pump 10 has its distal fitting 75 connected to a container or vessel which is to be evacuated, and the vacuum pump thereafter has its piston assembly 55 drawn proximally, frictional engagement between O-ring 85 and the inside surface of the cylinder's side wall 65 will cause O-ring 85 to move to the distal side of piston 80 so as to seal off the piston's axially-extending grooves 115 (FIGS. 13 and 14). As a result, the proximally-moving piston assembly 55 will draw air out of the aforementioned container or vessel and into the distal end of the cylinder, behind the retreating piston assembly. This action can be characterized as an "evacuation stroke".

Conversely, when vacuum pump 10 thereafter has its piston assembly 55 moved distally, frictional engagement between O-ring 85 and the inside surface of the cylinder's side wall 65 will cause O-ring 85 to move to the proximal side of piston 80 so as to open up the piston's axially-extending grooves 115. As a result, air on the distal side of piston assembly 55 will be able to pass by the distally-moving piston assembly to exit the proximal end of vacuum pump 10. This action can be characterized as an "exhaust stroke".

By placing one or more check valves in line between vacuum pump 10 and the container or vessel which is to be evacuated (e.g., one or more check valves 25 of the sort shown in FIG. 1), air can be permitted to pass out of the container or vessel and into vacuum pump 10 during the pump's evacuation stroke, but will be prevented from passing out of the pump and into the container or vessel during the pump's exhaust stroke.

In this way, repeated strokes of the vacuum pump's piston assembly 55 (activated manually via the piston rod's proximal end 125) can evacuate the gas in a container or vessel.

In one preferred aspect of the present invention, vacuum pump 10 is used in the aforementioned vacuum system 5 (FIG. 1) to create a vacuum in the container 20, whereby bone cement can be mixed under vacuum in that container. In connection with this particular application, and as noted above, vacuum system 5 preferably also comprises the vacuum indicator 15 for determining when the proper level of vacuum has been created in container 20, the pair of check valves 25 for preventing backflow of air from vacuum pump 10 into container 20, the filter 30 for preventing selected substances from passing from container 20 into vacuum pump 10, and the connector 35 adapted to make an airtight connection to the corresponding connector 40 provided on container 20. Flexible tubing 45 connects each of the foregoing elements together in series.

Figure 17:
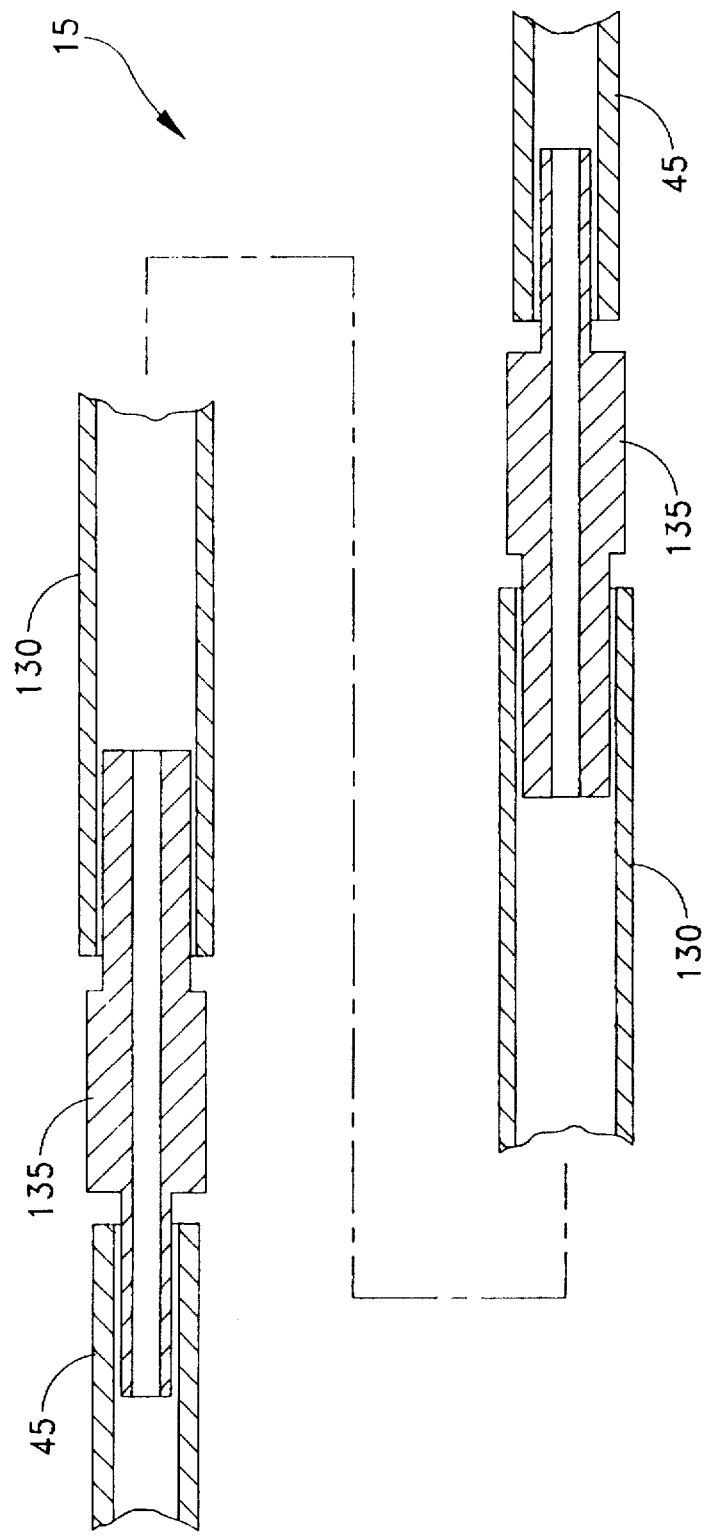
FIG. 17 is a schematic partial side view in section of the vacuum system's novel vacuum indicator.

Vacuum indicator 15 is shown in FIGS. 1 and 17. Vacuum indicator 15 comprises a tube 130 formed out of an elastomeric material such as latex rubber or Silastic silicone, and a pair of fittings 135 disposed on each end of tube 130. Fittings 135 are in turn connected to flexible tubing 45, whereby vacuum indicator 15 will be located inline between vacuum pump 10 and container 20. In this way the interior of vacuum indicator 15 will be at the same pressure as the interior of container 20, while the exterior of vacuum indicator 15 will be at ambient atmospheric pressure.

Vacuum indicator 15 is characterized by a substantially bi-state type of operation. This is in total contrast to prior art "drip chamber" vacuum indicators, which are characterized by an analog type of operation.

More particularly, with the novel vacuum indicator 15, so long as the pressure differential between the vacuum indicator's inside and outside environments is below a predetermined threshold, elastic tube 130 will retain its normal tubular shape. However, as soon as the pressure differential between the vacuum indicator's inside and outside environments exceeds that predetermined threshold, tube 130 will suddenly undergo a dramatic buckling of its wall, visually recognizable as the collapse of the tube. This is in contrast to prior art drip chamber vacuum indicators, which undergo a more gradual and more continuous sort of deformation as the pressure differential between the vacuum indicator's inside and outside environments builds.

Conversely, with the novel vacuum indicator 15, as soon as the pressure differential between the vacuum indicator's inside and outside environments once again falls below the aforementioned predetermined threshold, tube 130 will immediately return to its original tubular shape. Again, this is in marked contrast to prior art drip chamber vacuum indicators, which follow a more gradual and more continuous sort of restoration as the pressure differential between the vacuum indicator's inside and outside environments decreases.

Furthermore, with the novel vacuum indicator 15, as the vacuum indicator is thereafter cycled through a series of vacuums, the vacuum indicator will continue to change state at exactly the same level of pressure differential each time. Again, this is in marked contrast to prior art plastic drip chamber vacuum indicators which, as discussed above, tend to change their operating thresholds as the indicators cycle through sequential vacuums.

Part of the difference in operation between vacuum indicator 15 and prior art drip chamber vacuum indicators is due to the different materials they are made out of, i.e., while vacuum indicator 15 is formed out of an elastomeric material, the prior art drip chamber vacuum indicators are formed out of a plasticized material.

More particularly, the preferred elastomeric material is latex rubber or Silastic silicone where the mechanical behavior is such that the material remains elastic at a high strain rate (e.g., greater than 2%). In other words, the latex rubber or Silastic silicone material returns very rapidly its original shape and state even after undergoing a relatively large deformation. This is in significant contrast to prior art drip chamber vacuum indicators made out of a plasticized material such as polyvinylchloride (PVC) or polyvinylacetate or polyvinylalcohol or a similar material, where the plasticized material undergoes non-linear plastic deformation at a relatively low strain rate. In addition, such plasticized material may undergo permanent deformation even at relatively small strain levels. Furthermore, even if the plasticized material does not undergo permanent deformation, the plasticized material generally takes at least several minutes to return to its original shape and state after the deforming stress is released.

As noted above, part of the difference in operation between vacuum indicator 15 and prior art drip chamber vacuum indicators is due to the different materials they are made out of. However, part of the difference in operation between vacuum indicator 15 and prior art drip chamber vacuum indicators is due to differences in geometry. More particularly, vacuum indicator 15 is constructed so that its side wall is fairly thick relative to its radius, with a radius/thickness ratio of <5. This operates to minimize the effect of any wall imperfections or wall irregularities which may cause variations in operational behavior. In contrast, prior art drip chamber vacuum indicators typically have a side wall which is relatively thin relative to its radius, with a radius/thickness ratio of about 7–8. This makes prior art drip chamber vacuum indicators highly susceptible to wall imperfections or wall irregularities, which can cause variations in operational behavior.

The foregoing factors of material and geometry combine so as to cause the novel vacuum indicator 15 to undergo a totally different type of mechanical deformation than the prior art drip chamber vacuum indicators. More particularly, the material and geometry of vacuum indicator 15 causes it to undergo so-called "elastic buckling under hydrostatic pressure". In contrast, the material and geometry of prior art drip chamber vacuum indicators causes them to undergo so-called "plastic deformation under hydrostatic pressure".

It is possible to select the exact level of the pressure differential at which tube 130 will change state (i.e., from open to collapsed, or from collapsed to open) by changing the elastomeric material from which the tube is made, or by varying the tube's wall thickness, radius and, to a certain degree, length.

As noted above, experimental evidence has shown that it is most desirable to mix bone cement at a vacuum level of about 500–550 mm Hg. To this end, vacuum indicator 15 is preferably made out of latex or Silastic, and preferably has a length (between fittings 135) of approximately 25–50 mm, an outer diameter of approximately 7.6 mm, and an inner diameter of about 4.7 mm.

Check valves 25 prevent backflow of air from vacuum pump 10 into container 20. Check valves 25 may be any of the many check valve designs well known in the art. By way of example, but not limitation, check valves 25 might be disk-type check valves or duckbill-type check valves. Preferably two check valves 25 are provided in the system, although it is also anticipated that only one check valve 25 might be provided in the system, or more than two check valves 25 might be provided in the system.

As shown in FIG. 1, it is preferred that check valves 25 be positioned between vacuum pump 10 and filter 30. However, it is also possible to position check valves 25 elsewhere in the vacuum line extending from container 20 to vacuum pump 10, provided, however, that at least one check valve 25 is located on the vacuum pump side of vacuum indicator 15.

Filter 30 serves to prevent selected substances from passing from container 20 into vacuum pump 10. In the bone cement application shown in FIG. 1, filter 30 is intended to prevent free monomer fumes, exiting container 20, from passing out vacuum pump 10 and into the ambient atmosphere. In addition, filter 30 is intended to prevent polymer powders from passing out of container 20 and into check valves 25 and/or vacuum pump 10, where they may undermine the performance of these elements. Finally, in the bone cement application shown in FIG. 1, filter 30 may also serve to prevent bacterial or other contaminates from passing through the vacuum line and into container 20. Filters capable of satisfying the foregoing requirements are well known in the art. For example, filter 30 might comprise a charcoal filter.

Connector 35, located on the distal end of the vacuum line, and connector 40, located on container 20, may comprise any one of the many connector sets well known in the art. Such connector sets typically utilize a male-female coupling, with connector 40 including some sort of check valve arrangement so as to render connector 40 self-sealing when it is not being engaged by connector 35. By way of example, connector 35 might comprise something equivalent to the blunt inflation pump cannulas of the type commonly used to inflate an ordinary basketball or football, and connector 40 might comprise something equivalent to the rubber self-sealing inflation ports used on such basketballs and footballs. Alternatively, connector 35 and connector 40 might comprise a Clave™ valve Needleless Connecter (ICU Medical Inc., Irvine, Calif.), or an InterLink™ System (Baxter Healthcare Corporation, Deerfield, Ill.) injection port with pre-slit septum in combination with an InterLink™ cannula (Becton Dickinson & Co., Franklin Lake, N.J.). For the purposes of the present invention, the only requirements for connector 35 and connector 40 is that (i) they are capable of making an airtight connection when they are in engagement with one another, and (ii) connector 40 is self-sealing when connector 35 (and hence the distal end of the vacuum line) is disconnected from connector 40.

Vacuum system 5 is used as follows. First, the system is set up by placing the bone cement's constituent monomer and polymer components into container 20. Then the vacuum line is assembled together, whereby the distal end of the vacuum line is connected to container 20 and the proximal end of the vacuum line is connected to vacuum pump 10, with vacuum indicator 15, check valves 25 and filter 30 disposed therebetween. When the user is ready to mix cement, the vacuum pump is operated by using the proximal end 125 of piston rod 60 to move piston assembly 55 back and forth within cylinder 50. This action will move piston assembly 55 through an alternating series of evacuation and exhaust strokes. As this occurs, air will be evacuated from container 20 and, via the open end of vacuum pump 10, vented to the ambient atmosphere.

As noted above, flexible tubing 45 is used to connect together various elements of the vacuum system (i.e., vacuum pump 10, vacuum indicator 15, check valves 25, filter 30 and connector 35). It is to be appreciated that flexible tubing 45 is formed so as to be strong enough to resist collapse when subjected to the vacuum levels associated with the present invention. Flexible tubing 45 is preferably formed out of polyvinylchloride (PVC). At the same time, however, air will not be able to return to container 20 (via the open end of vacuum pump 10) due to the presence of check valves 25 in the vacuum line. The user continues to operate vacuum pump 10 until the resilient tube 130 of vacuum indicator 15 collapses. At this point the vacuum in container 20 will be at the proper level for mixing bone cement. The bone cement in container 20 is then mixed in ways well known in the art.

Among other things, it is to be appreciated that the highly efficient nature of vacuum pump 10 permits the pump to be operated manually so as to establish the desired level of vacuum in container 20, yet without causing undue fatigue on the part of the operator.

Modifications of the Preferred Embodiments

It is, of course, possible to modify the preferred embodiments of the present invention without departing from the scope of the present invention.

Thus, for example, more or less than two check valves 25 might be incorporated into vacuum system 5. Furthermore, it is anticipated that more than one filter 30 might be provided in vacuum system 5.

Figures 18, 19:
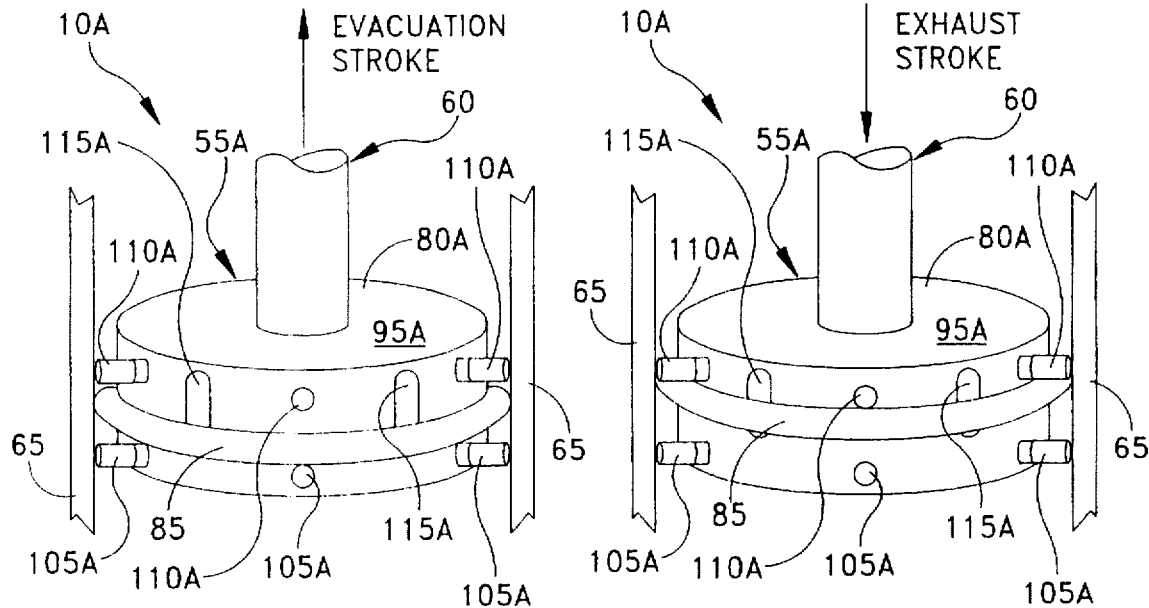
FIG. 18 is a perspective side view of an alternative form of piston assembly formed in accordance with the present invention, with the piston assembly being shown during the vacuum pump's evacuation stroke.
FIG. 19 is a perspective side view of the piston assembly shown in FIG. 18, but with the piston assembly being shown during the vacuum pump's exhaust stroke.
Figures 20, 21:
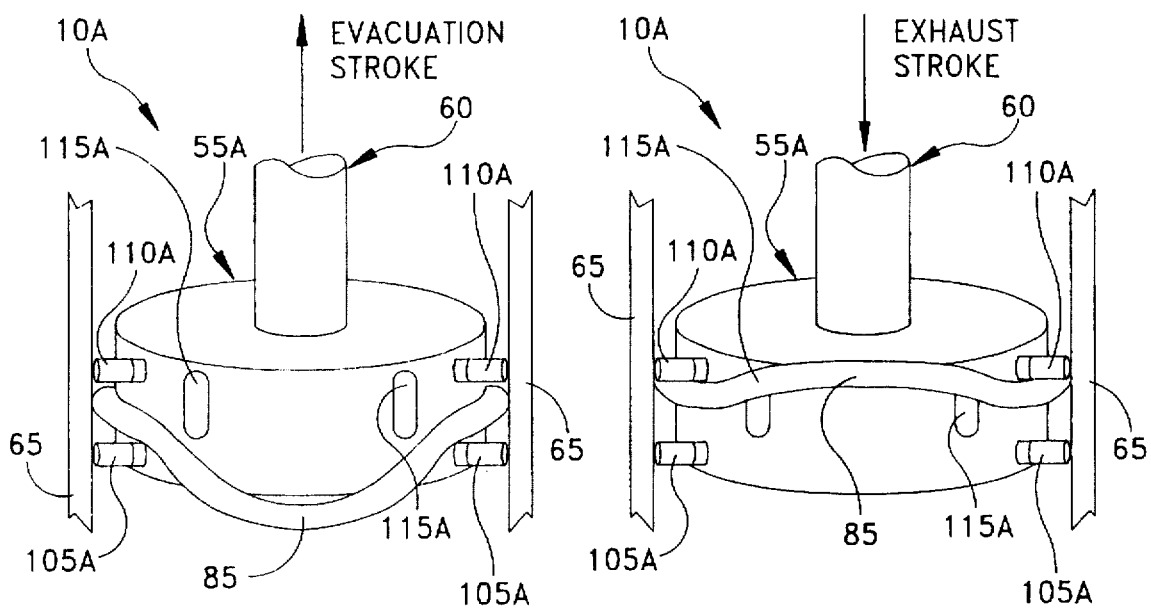
FIG. 20 is a perspective side view of still another form of piston assembly, with the piston assembly being shown during the vacuum pump's evacuation stroke.
FIG. 21 is a perspective side view of the piston assembly shown in FIG. 20, but with the piston assembly being shown during the vacuum pump's exhaust stroke.

It is also possible to modify the construction of vacuum pump 10 without departing from the scope of the present invention. For example, and looking now at FIGS. 18 and 19, a vacuum pump 10A having a piston assembly 55A might be provided. Piston assembly 55A is substantially the same as the piston assembly 55 described above, except as will hereinafter be described in detail. More particularly, piston assembly 55A comprises a piston 80A and an O-ring 85. A plurality of circumferentially-aligned distal stops 105A limit the distal movement of O-ring 85 along the outer surface of piston 80A (FIG. 18). A plurality of circumferentially-aligned proximal stops 110A limit the proximal movement of O-ring 85 along the outer surface of piston 80A (FIG. 19). A plurality of axially-extending surface grooves 115A are formed in the outer surface of piston 80A. The distal ends of surface grooves 115A terminate on the proximal side of circumferentially-aligned distal stops 105A, and the proximal ends of surface grooves 115A terminate on the proximal side of circumferentially-aligned proximal stops 110A. In this way, piston assembly 55A will (i) prevent air from moving past the piston assembly during an evacuation stroke (i.e., as the piston assembly is moved proximally), and (ii) not prevent air from moving past the piston assembly during an exhaust stroke (i.e., as the piston assembly is moved distally). It is to be appreciated that the proximal ends of axially-extending surface grooves 115A need not open on the piston's proximal end surface 95A; rather, it is sufficient for the distal ends of axially-extending surface grooves 115A to terminate proximally of circumferentially-aligned proximal stops 110A. It is also to be appreciated that, with the particular construction of vacuum pump 10A, it is important that stops 105A and 110A be sufficient in number to properly support O-ring 85. If too few stops 105A and/or 110A are provided, O-ring 85 may flex in the manner shown in FIGS. 20 and 21, which can inhibit proper sealing.

Figure 23:
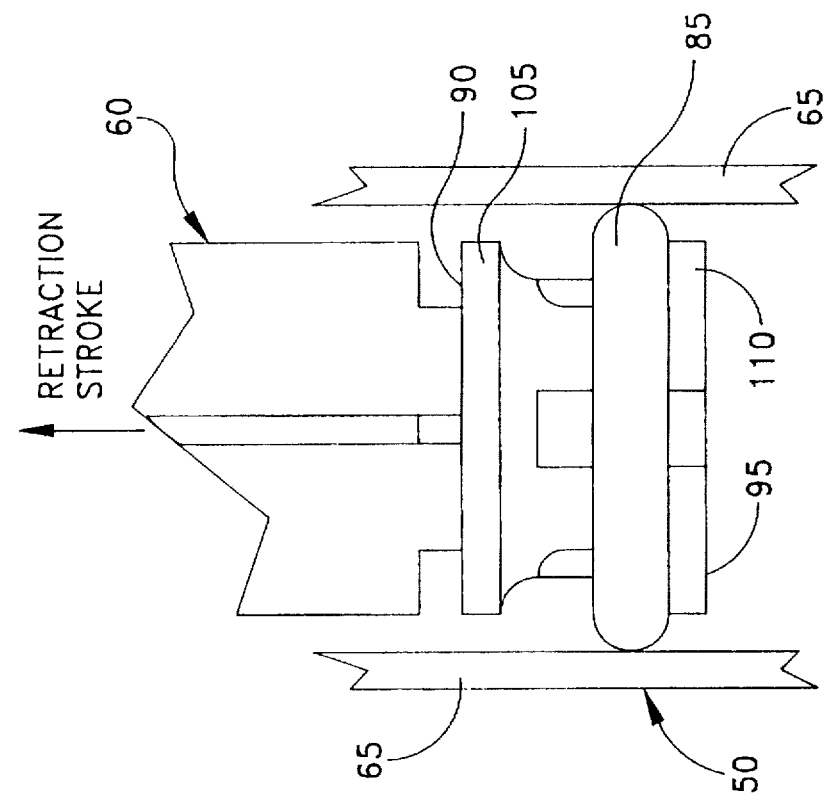
FIG. 23 is a schematic side view like that of FIG. 22, except with the pressurizing pump being shown in a retraction (i.e., air gathering) stroke.
Figure 22:
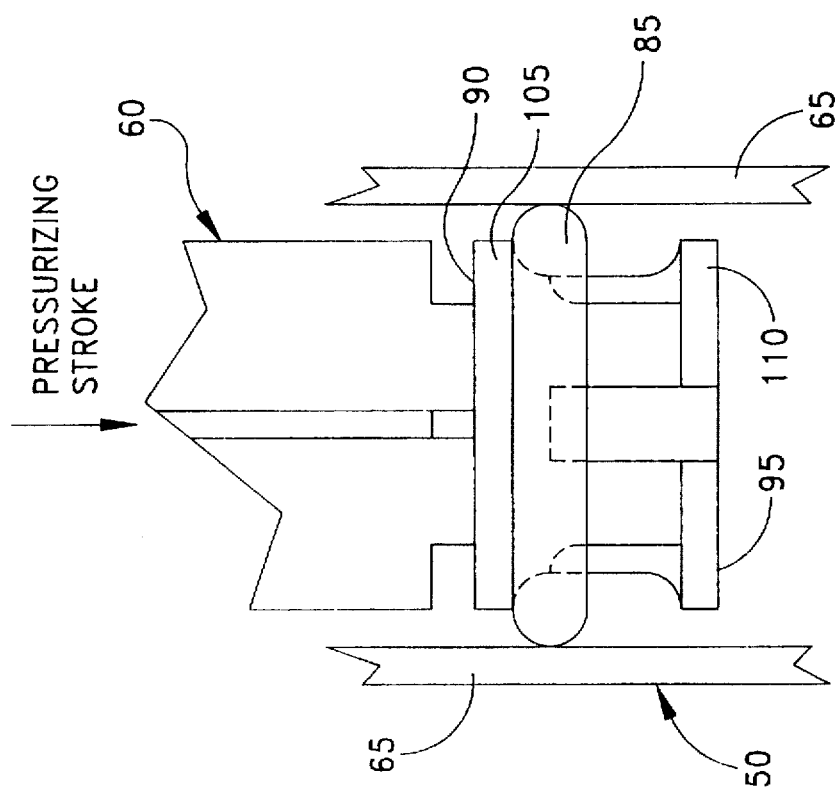
FIG. 22 is a schematic side view of selected portions of a pressurizing pump formed in accordance with the present invention, with the pressurizing pump being shown in a pressurizing (i.e., air pushing) stroke.

It is also possible to modify vacuum pump 10 so that it will act as a pressurizing pump. More particularly, vacuum pump 10 can be converted into a pressurizing pump by reversing the orientation of piston assembly 55 relative to piston rod 60, i.e., so that shoulder 105 is adjacent to piston rod 60 and shoulder 110 is remote from piston rod 60. Thus, FIG. 22 shows such a pressurizing pump 10B during a pressurizing (i.e., air pushing) stroke, whereas FIG. 23 shows such a pressurizing pump 10B during a retraction (i.e., air gathering) stroke. To the extent that pressurizing pump 10B is to be used to pressurize a container or vessel, it should be appreciated that a check valve (e.g., a check valve such as the check valve 25 discussed above) should be disposed between the pressurizing pump and the container or vessel. Of course, in such a situation, the check valve 25 will have its orientation reversed from the orientation shown in the vacuum system of FIG. 1, whereby the check valve in the pressurizing system will permit air to pass from the pressuring pump to the container or vessel, but will prohibit air from passing from the container or vessel to the pump.

Also, it should be appreciated that while the foregoing vacuum pump 10 and 10A, and the foregoing pressurizing pump 10B, have generally been discussed in the context of moving a gas, they could also be used to move a liquid. In essence, pumps 10, 10A and 10B are fluid pumps capable of moving gases and/or liquids.

It is also possible to provide a vacuum system like that shown in FIG. 1, except incorporating a plurality of different vacuum indicators 15 disposed in parallel, where each vacuum indicator is adapted to collapse at a different level of vacuum. Since each vacuum indicator 15 is capable of assuming only one of two states (i.e., fully open or fully collapsed) such an arrangement can be used to provide a better indication of the level of the vacuum in the system. More particularly, by noting exactly which vacuum indicators 15 are in their collapsed state and which vacuum indicators 15 are in their fully open state, the observer may be better able to ascertain the current level of vacuum in the system at any given time.

Still other modifications will be obvious to a person skilled in the art, and are considered to fall within the scope of the present invention.

Advantages Of The Invention

Numerous advantages are achieved by the present invention.

For one thing, the present invention provides a new and improved vacuum system for creating a vacuum within a container or vessel.

For another thing, the present invention provides a new and improved vacuum system which is particularly well suited for use in connection with bone cement mixing systems.

And the present invention provides a new and improved vacuum pump.

Also, the present invention provides a new and improved vacuum pump which is particularly well suited for use in connection with bone cement mixing systems.

Furthermore, the present invention provides a new and improved vacuum indicator.

And the present invention provides a new and improved vacuum indicator which is particularly well suited for use in connection with bone cement mixing systems.

And the present invention provides a new and improved method for creating a vacuum within a container or vessel.

And the present invention provides a new and improved method for creating a vacuum within a container or vessel in a bone cement mixing system.

What is claimed is:

1. A vacuum indicator comprising:

an elongated tubular member for disposal in a vacuum line between a vacuum producer and a container to be evacuated, such that the interior of said tubular member is at the same pressure as the interior of the container, and the exterior of said tubular member is at atmospheric pressure, said tubular member being of a non-plastics elastomeric material;

a wall of said tubular member having a uniform thickness of greater than ⅕ of an inside radius of said tubular member; said wall material and thickness being such, in combination, that upon reaching a predetermined differential in said interior and exterior pressures, said tubular member undergoes sudden collapse, while said vacuum line remains in a substantially unaltered state.

2. A vacuum indicator according to claim 1 wherein said elastomeric material is selected from a group of materials consisting of latex rubber and Silastic silicone.

3. A vacuum indicator according to claim 1 wherein said elastomeric material comprises a bi-state elastic material, such that until said predetermined differential in pressures is attained in said tubular member, said member retains a first fully open configuration, and upon said predetermined differential in pressures being attained in said tubular member, said member undergoes said sudden collapse, and upon loss of said predetermined pressure differential, said member regains said first configuration, whereby to provide a visible indication as to the attainment and loss of said preselected vacuum in said tubular member, and thereby said vacuum line and said container.

4. A vacuum pump assembly for establishing a vacuum in a container, said assembly comprising:

a vacuum pump;

transfer means interconnecting said vacuum pump and said container; and a vacuum indicator disposed in said transfer means;

said vacuum pump comprising means for establishing vacuum in said transfer means;

said transfer means comprising:
- a conduit extending from said vacuum pump to said container, said conduit having one-way check valve means therein, such that a vacuum attained in said vacuum pump is extended to said container; and said vacuum indicator comprising:
- an elongated tubular member for disposal in said conduit between said vacuum pump and said container, said tubular member being of an elastomeric material and suddenly and instantly collapsible upon attainment of a preselected vacuum therein; and
- a wall of said tubular member having a uniform thickness of greater than 1/5 of an inside radius of said tubular member;
- said wall material and said wall thickness being such, in combination, as to provide said sudden and instant collapse upon said attainment of said preselected vacuum.

5. A method for establishing a vacuum in a container, said method comprising the steps of:

providing a vacuum pump;

providing transfer means for interconnecting said vacuum pump and said container; and providing a vacuum indicator for use in said transfer means;

said vacuum pump comprising means for establishing a vacuum in said transfer means;

connecting said vacuum pump to said transfer means, and said transfer means to said container, said transfer means comprising:
- a conduit extending from said vacuum pump to said container, said conduit having one-way check valve means therein, such that a vacuum attained in said vacuum pump is extended to said container;

inserting said vacuum indicator in said conduit, said vacuum indicator comprising:
- an elongated tubular member of an elastomeric material and suddenly and instantly collapsible upon attainment of a preselected vacuum therein, and a wall of said tubular member having a uniform thickness of greater than 1/5 of an inside radius of said tubular member, said tubular member wall material and thickness being such, in combination, as to provide said sudden and instant collapse upon said attainment of said preselected vacuum; and operating said vacuum pump so as to establish a vacuum in said container, until collapse of said tubular member.

* * * * *